(12) United States Patent
Miller et al.

(10) Patent No.: US 8,735,633 B2
(45) Date of Patent: May 27, 2014

(54) METHODS FOR MAKING 1,3-DIHYDROXYACETONE (DHA) FROM GLYCEROL

(75) Inventors: Dennis Miller, Okemos, MI (US); Xi Hong, Lansing, MI (US); Carl Lira, East Lansing, MI (US); Omar McGiveron, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 146 days.

(21) Appl. No.: 13/183,114

(22) Filed: Jul. 14, 2011

(65) Prior Publication Data

US 2012/0014889 A1    Jan. 19, 2012

Related U.S. Application Data

(60) Provisional application No. 61/364,069, filed on Jul. 14, 2010.

(51) Int. Cl.
| | |
|---|---|
| A61K 31/401 | (2006.01) |
| A61K 8/35 | (2006.01) |
| A61Q 15/00 | (2006.01) |
| A61Q 17/04 | (2006.01) |
| A61Q 19/00 | (2006.01) |
| C07C 45/42 | (2006.01) |

(52) U.S. Cl.
USPC ............... 568/391; 424/59; 424/65; 514/423; 568/405

(58) Field of Classification Search
None
See application file for complete search history.

(56) References Cited

U.S. PATENT DOCUMENTS

| | | | |
|---|---|---|---|
| 5,770,411 A | 6/1998 | Ohrem et al. | |
| 7,321,052 B2 * | 1/2008 | Miller et al. | 560/231 |
| 2005/0233423 A1 | 10/2005 | Berka et al. | |
| 2006/0177917 A1 | 8/2006 | Warzywoda et al. | |
| 2009/0061486 A1 | 3/2009 | Edwards et al. | |

FOREIGN PATENT DOCUMENTS

WO    WO-2007005918 A2    1/2007

OTHER PUBLICATIONS

Deutsch (Deutsch et al., Investigations on heterogeneously catalyzed condensations of glycerol to cyclic acetals, J. Catal., 245 (2007) 428-438).*
Hu, Wenbin, et al., "Catalytic Oxidation of Glycerol to Dihydroxyacetone", 21st International Symposium on Chemical Reaction Engineering, ISCRE 21, Philadelphia, PA, (2010), Abstract 256.
Hu, Wenbin, et al., "Catalytic Oxidation of Glycerol to High-Value Chemical Dihydroxyacetone", 21st North American Catalysis Society Meeting, San Francisco, CA, (2009), OA15.
Hu, Wenbin, et al., "Selective Oxidation of Glycerol to High-Value Chemical Dihydroxyactone over Pt-Bi/C Catalyst", 09AlChE Annual Meeting, Nashville, TN, (Nov. 9, 2009), 27 pgs.
Piancatelli, G., et al., "Pyridinium Chlorochromate: A Versatile Oxidant in Organic Synthesis", Georg Thieme Verlag, (Apr. 1982), 245-258 and 1164.
Sukumaran, R. K, et al., "Cellulase production using biomass feed stock and its application in lignocellulose saccharification for bioethanol production", Renewable Energy, 34(2), (Feb. 2009), 421-424.

* cited by examiner

*Primary Examiner* — Daniel Sullivan
*Assistant Examiner* — Dominic Lozaro
(74) *Attorney, Agent, or Firm* — Clark IP Law, PLC

(57) ABSTRACT

A method comprising reacting glycerol with acetaldehyde or 1,1-diethoxyethane to produce 1,3-dihydroxyacetone (DHA), without using fermentation or direct oxidation of the glycerol is provided. DHA is useful in various products, including as a sunless tanning agent.

28 Claims, 3 Drawing Sheets

METHODS FOR MAKING 1,3-DIHYDROXYACETONE (DHA) FROM GLYCEROL

This application claims priority under 35 U.S.C. 119(e) to U.S. Provisional Patent Application Ser. No. 61/364,069 filed Jul. 14, 2010, which is hereby incorporated herein by reference in its entirety.

GOVERNMENT RIGHTS

This invention was made with government support under 2006-35504-17364, awarded by the U.S. Department of Agriculture. The government has certain rights in the invention.

BACKGROUND 1,3-Dihydroxyacetone, commonly referred to as dihydroxyacetone (DHA), is used as an ingredient in sunless tanning products and in the food preparation industry. DHA is often produced using fermentation methods. Conventional DHA production methods have low productivity and high production costs.

SUMMARY

The inventors recognize a need for providing DHA in a more cost efficient manner. In one embodiment, a method comprising reacting glycerol with acetaldehyde or 1,1-diethoxyethane to produce 1,3-dihydroxyacetone (DHA), without using fermentation or direct oxidation of the glycerol is provided. In one embodiment, DHA is produced in a batch process in less than 20 hours. In one embodiment, the DHA is produced in a continuous process.

In one embodiment, selectivity or yield of the DHA is greater than about 50%, such as greater than about 80% or higher. The method can further comprise, in one embodiment, forming glycerol acetal isomers from the glycerol and acetaldehyde or 1,1-diethoxyethane with an acid catalyst (e.g., sulfuric acid), wherein at least one of the glycerol acetal isomers is a cis-5-hydroxy-2-methyl-1,3-dioxane isomer (cis-6 isomer); separating the cis-6 isomer from the glycerol acetal isomers; and with an oxidation catalyst, oxidizing the cis-6 isomer to produce 2-methyl-1,3-dioxan-5-one (G-tone). The oxidizing step can, in some embodiments, further comprise adding an oxidizer such as $KBrO_3$, $NaBrO_3$, $NaClO$, $Ca(ClO)_2$ or $NaIO_4$.

In one embodiment, the glycerol acetal isomers further comprise trans-5-hydroxy-2-methyl-1,3-dioxane (trans-6 isomer), cis-4-hydroxymethyl-2-methyl-1,3-dioxolane (cis-5 isomer), and trans-4-hydroxymethyl-2-methyl-1,3-dioxolane (trans-5 isomer), wherein the method further comprises converting the trans-6 isomer, the cis-5 isomer, the trans-5 isomer, or combinations thereof, to the cis-6 isomer.

The oxidation catalyst can be a homogeneous catalyst or a heterogeneous catalyst. In one embodiment, the oxidation catalyst is a ruthenium catalyst (e.g., ruthenium (III) trichloride catalyst, a ruthenium dioxide catalyst, ruthenium tetraoxide catalyst, and the like), a palladium catalyst or a platinum catalyst.

Embodiments further include a method comprising combining glycerol and acetaldehyde in a first reactor to produce glycerol acetal isomers and water together with unreacted acetaldehyde; separating the glycerol acetal isomers from the unreacted acetaldehyde and water in an evaporator; distilling the glycerol acetal isomers in a vacuum distillation column with an acid catalyst; removing cis-5-hydroxy-2-methyl-1,3-dioxane isomer (cis-6 isomer) from the vacuum distillation column; oxidizing the cis-6 isomer in a second reactor to produce 2-methyl-1,3-dioxan-5-one (G-tone); and combining the G-tone with water in a reactive distillation column to produce 1,3-dihydroxyacetone (DHA). In one embodiment, the glycerol acetal isomers are continuously interconverted within the vacuum distillation column.

The method can further comprise removing less volatile glycerol acetal isomers from the reboiler of the vacuum distillation column; heating the less volatile glycerol acetal isomers to produce heated isomers; exposing the heated isomers to an acid catalyst in a third reactor to produce equilibrated isomers; and combining the equilibrated isomers with glycerol acetal isomers exiting the evaporator. In one embodiment, the unreacted acetaldehyde and water are separated in a vaporizer using flash distillation. The separated acetaldehyde can be provided to the first reactor.

Products produced according to the novel methods described herein can include a tanning agent, a skin conditioner, a fragrance, or an anti-perspirant, each of which can include an effective amount of DHA to accomplish the desired purpose (e.g., tanning, conditioning, and the like) in combination with a suitable carrier. In one embodiment, the product further comprises proline.

Embodiments described herein utilize a new process which can significantly improve the productivity of DHA from glycerol. The methods described herein are suitable for carrying out the processes on a large scale.

DETAILED DESCRIPTION

Figure 1:
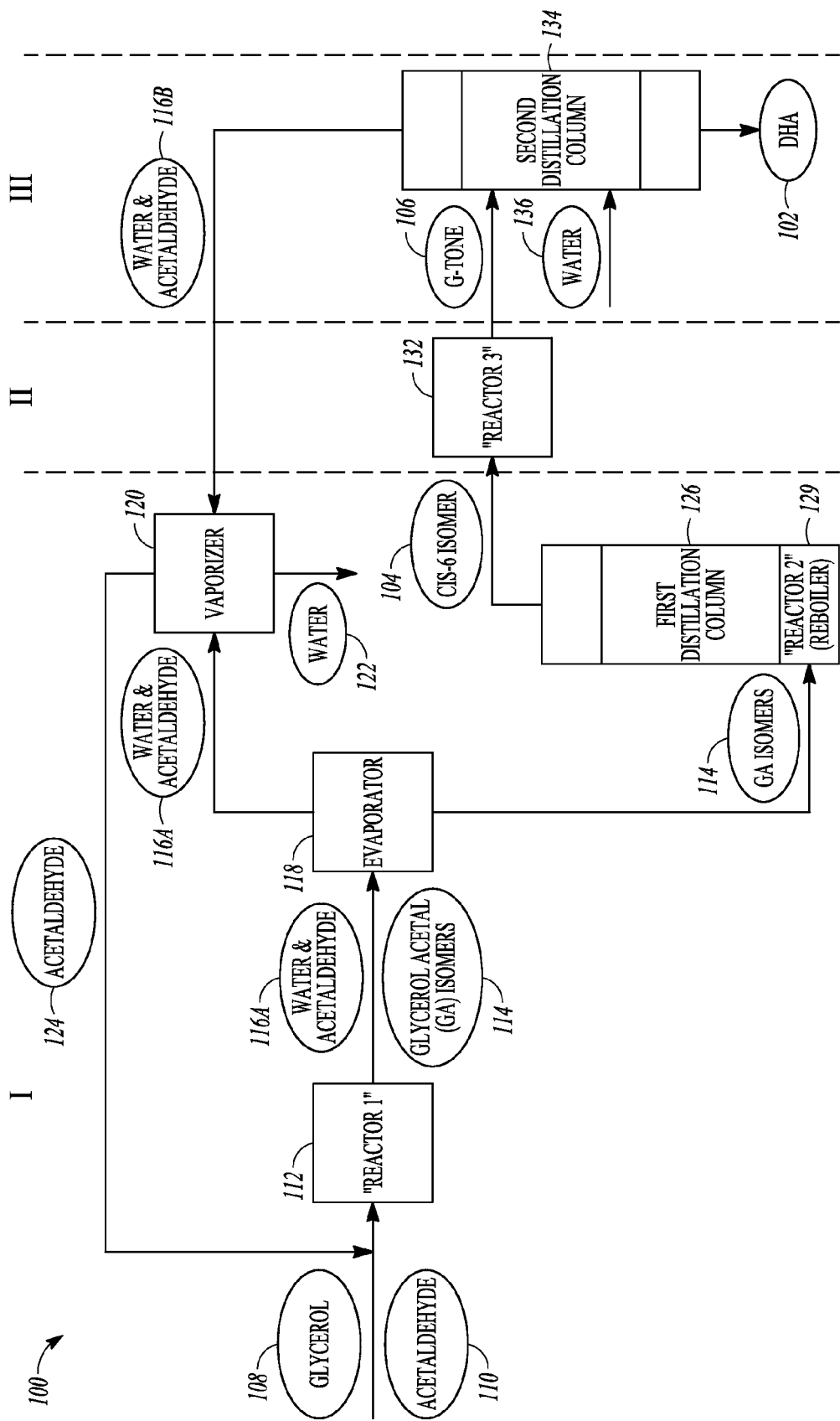
FIG. 1 illustrates a process for production of 1,3-Dihydroxyacetone (DHA) according to an embodiment.

In the following detailed description, various embodiments are described in sufficient detail to enable those skilled in the art to practice them. It is to be understood that other embodiments may be utilized and that chemical and procedural changes may be made without departing from the spirit and scope of the present subject matter. The following detailed description is, therefore, not to be taken in a limiting sense, and the scope of embodiments is defined only by the appended claims.

The Detailed Description that follows begins with a definition section followed by a brief background discussion, a description of the embodiments, examples and a conclusion.

DEFINITIONS

The term "carrier" as used herein refers to a component that, when combined with a DHA-containing compound, produces a composition that can be applied as a topical agent to the skin (e.g., for sunless tanning, cosmetic, or medicinal purposes), ingested as a neutraceutical composition, distributed or applied as a fungicidal composition to a target area, or used as a plasticizer. A carrier can include, but is not limited to various liquids, solids and gases. This includes, but is not limited to, oils, including any type of vegetable oils, such as canola oil, soybean oil, and so forth, polymers, such as slow-release polymers, plastics, waxes, wood, gels, colloids (e.g., creams and lotions), granular materials, such as clays and minerals (e.g., vermiculite, bentonite), dusts, powders, sprays, drenching means, emulsifiable concentrates, and so forth. This can further include products such as misters or aerosol sprays. The choice of carrier depends on several factors, including, but not limited to, the specific need.

The term "neutraceutical" as used herein, refers to edible materials having, or believed to have, medicinal effects. Nutraceuticals include the tocopherols, B vitamins, ginseng and other herbs, wheat grass and barley grass and extracts of the grasses, soy-based estrogen analogs, minerals and so on.

The term "biodiesel" as used herein, refers to a vegetable oil- or animal fat-based diesel fuel consisting of long-chain alkyl methyl esters. Biodiesel is typically made by chemically reacting lipids (e.g., vegetable oil, animal fat (tallow) with an alcohol).

Background on 1,3-dihydroxyacetone (DHA)

Glycerol, which is produced as a by-product of biodiesel production, is a useful starting material for DHA. Conventional production of DHA from glycerol fermentation requires reaction times longer than 20 hours, or higher, such as up to about 70 hours, with relatively low yields (i.e., about 40% or lower). Conventional production of DHA via direct oxidation requires noble metals, such as platinum and gold, with selectivity for DHA no higher than 50%.

Discussion of Embodiments

In one embodiment, a novel method for producing 1,3-dihydroxyacetone (DHA) from glycerol according to the method shown in Scheme 1 is provided:

Scheme 1

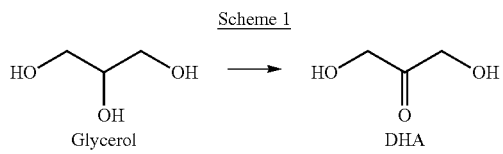

Glycerol                DHA

In one embodiment, glycerol is reacted with acetaldehyde or 1,1-diethoxyethane under suitable conditions to form four glycerol acetal (GA) isomers and water. One of the isomers, namely the cis-5-hydroxy-2-methyl-1,3-dioxane isomer (hereinafter "cis-6 isomer") is then oxidized to its ketone counterpart, 2-methyl-1,3-dioxan-5-one (G-tone). It is expected that DHA can be recovered from the G-tone through hydrolysis and separation. (See Example 1).

In one embodiment, as discussed in Example 2, acetaldehyde is used. In this embodiment, glycerol is reacted with acetaldehyde under suitable conditions to form GA and water as shown in Scheme II. Unreacted glycerol and acetaldehyde may also be present.

Scheme II

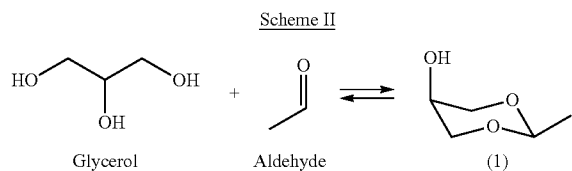

Glycerol    Aldehyde         (1)

+

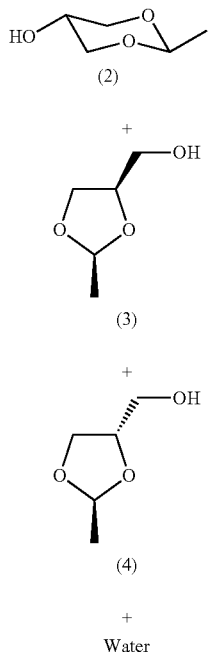

+

Water

The GA isomers shown in Scheme II include (1) the cis-6 isomer, (2) trans-5-hydroxy-2-methyl-1,3-dioxane (hereinafter "trans-6 isomer"), (3) cis-4-hydroxymethyl-2-methyl-1,3-dioxolane (hereinafter "cis-5 isomer"), and (4) trans-4-hydroxymethyl-2-methyl-1,3-dioxolane (hereinafter "trans-5 isomer") wherein the cis-6 isomer is the most volatile isomer amongst the four isomers. (See also Step I in FIGS. 1 and 2). In contrast to conventional methods using fermentation or direct oxidation techniques, the novel methods described herein utilize acid catalysts, such as a Brønsted acid catalysts, (for GA formation and for interconversion of the resulting four glycerol acetal isomers to cis-6) prior to using an oxidation catalyst to convert cis-6 to G-tone) to produce high yields of DHA in a relatively short amount of time. In one embodiment, the DHA is produced in a batch process in less than 20 hours at a yield in excess of 50%. In one embodiment, DHA is produced continuously without direct oxidation or fermentation.

In one embodiment, the cis-6 isomer is oxidized to its ketone counterpart, i.e., G-tone, as shown in Scheme III (See also Step II in FIGS. 1 and 2):

Scheme III

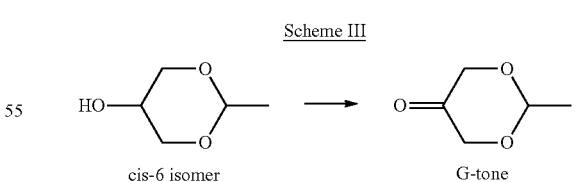

cis-6 isomer            G-tone

In one embodiment, the cis-6 isomer is converted to G-tone with use of any suitable type of homogeneous or heterogeneous oxidation catalyst. In one embodiment, a chromium-based catalyst is used (e.g., pyridinium chlorochromate). (See Example 5). In other embodiments, various ruthenium catalysts are used, including, but not limited to, ruthenium (III) trichloride, ruthenium dioxide, ruthenium tetraoxide, and the like. In yet other embodiments, various platinum or palladium catalysts are used. In yet other embodiments, various oxidizers are used in combination with the catalysts, including but not limited to, KBrO$_3$, NaBrO$_3$, NaClO, Ca(ClO)$_2$, NaIO$_4$ and the like. (See Examples 6-12).

It is expected that DHA can be recovered through use of hydrolysis (with an acid catalyst) and separation as shown in Scheme IV and described in prophetic Examples 13 and 14 (See also Step III in FIGS. 1 and 2):

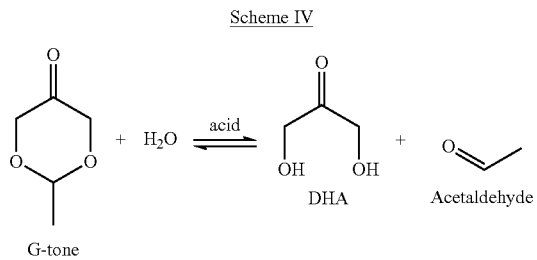

Scheme IV

The various methods described herein can provide high yields of DHA, of at least 40% up to 50% or greater, such as up to 60%, 70%, 80%, 90%, or higher, up to quantitative amounts of DHA, including any range there between. In one embodiment, DHA is produced from G-tone at elevated temperatures and under vacuum, although the invention is not so limited. See, for example the various temperature and pressure combinations discussed in the Examples. Additionally, it may be possible to use other temperature and pressure combinations, further including a wider range of temperatures during each of the various steps described herein.

FIG. 1 illustrates an exemplary method 100 for producing DHA 102. The method comprises producing the cis-6 isomer 104 (together with other GA isomers) in Step I, oxidation of the cis-6 isomer 104 to produce G-tone 106 in Step II, and hydrolysis and separation of G-tone 106 in Step III to produce the DHA 102.

In the embodiment shown in FIG. 1, Step I comprises combining glycerol 108 and acetaldehyde 110 in a reactor, such as "reactor 1" 112, under conditions adapted to produce glycerol acetal isomers (GA isomers) 114 and product water and unreacted acetaldehyde, "water and acetaldehyde" 116A, and some unreacted glycerol. The conditions useful for this reaction can vary depending on the amount of acetaldehyde added. In one embodiment, conditions are favorable for producing only trace amounts of unreacted glycerol. In one embodiment, varying amounts of acetaldehyde can be added under temperatures ranging from about 0° C. to about 70° C.

GA isomers 114 and the "water and acetaldehyde" 116A are then separated in an evaporator 118. Thereafter, the "water and acetaldehyde" 116A are provided to a vaporizer 120 where they are separated to produce water 122 and acetaldehyde 124, with the acetaldehyde 124 recycled back to "reactor 1" 112 as shown. In one embodiment, flash distillation (i.e., equilibrium flash vaporization) is used to separate the water 122 and acetaldehyde 124.

Thereafter, the GA isomers 114 are distilled in a first distillation column 126 (e.g., vacuum distillation column) containing a suitable acid catalyst as described herein, in which the most volatile isomer, the cis-6 isomer 104 is continuously drawn off the top. In one embodiment, the temperature and pressure of the first distillation column 126 are maintained at levels sufficient to allow the GA isomers 114 to be continuously interconverted (i.e., maintained in equilibrium) within the reboiler 129. In one embodiment, the reactive distillation occurs at elevated temperatures, such as at least about 80° C., although the invention is not so limited. In one embodiment, the reactive distillation occurs under vacuum.

In the embodiment shown in FIG. 1, the reboiler 129 portion of the first distillation column 126 is essentially serving as a reactor, namely "Reactor 2." In this embodiment, therefore, distillation occurring within the first distillation column 126 is designed to be relatively slow, in order to allow the GA isomers 114 to remain in chemical equilibrium within the reboiler 129. In one embodiment, conditions are provided to allow only cis-6 isomer to be withdrawn from the top of the column. The actual rate depends on several factors, such as scale of process, catalyst amount, and the like. In one embodiment the slow distillation in this embodiment occurs at a rate of no more than about 0.5 to about 1.5 ml/min. Over time, the amount of cis-6 isomer 104 drawn off the top of the first distillation column 126 is reduced, as the GA isomers 114 within the first distillation column 126 contain an increasingly reduced amount of the cis-6 isomer 104.

As FIG. 1 shows, Step II begins with providing the recovered cis-6 isomer 104 to "Reactor 3" 132 to oxidize the cis-6 isomer 104 to produce G-tone 106 as described herein.

Step III begins with providing the G-tone 106 to a second distillation column (e.g., reactive distillation column 134), where it is combined with water 136 to produce the DHA 102 and "water and acetaldehyde" 116B, the latter of which is returned to the vaporizer 120 (in Step I) where it is separated into water 122 and acetaldehyde 124 as described above.

Figure 2:
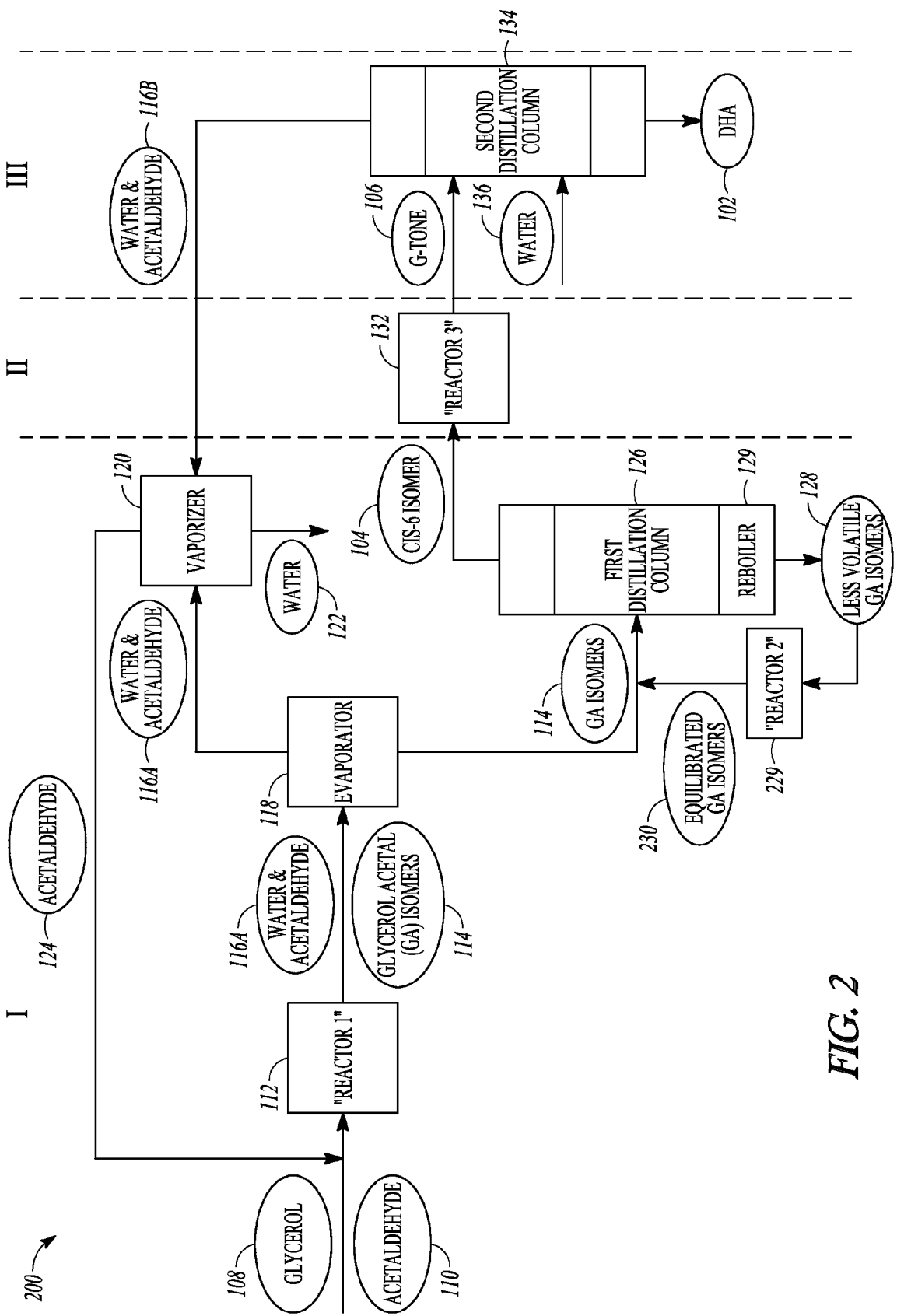
FIG. 2 illustrates an alternative process for production of DHA according to an embodiment.
Figure 3:
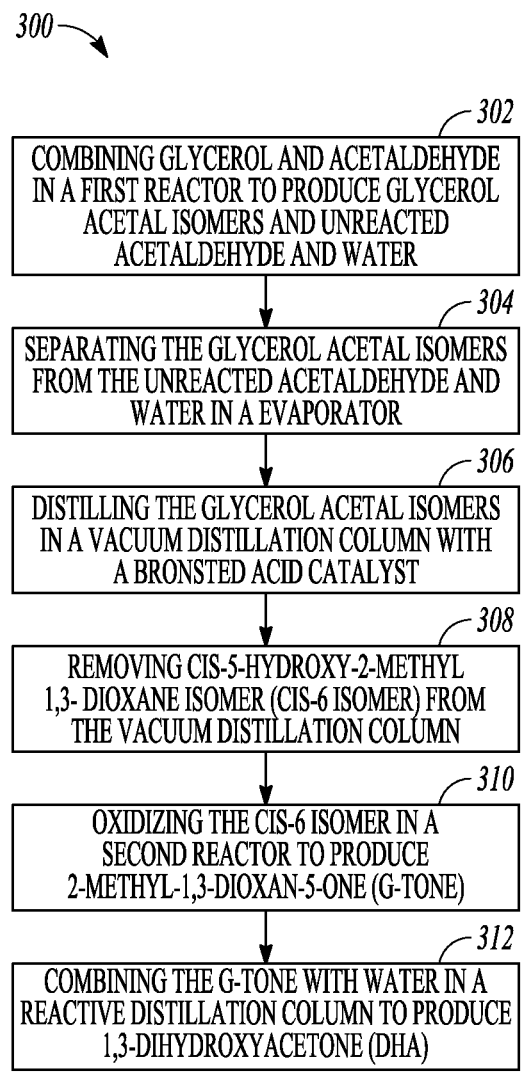
FIG. 3 is a flow diagram according to an embodiment.

FIG. 2 shows an alternative method 200 which includes the steps noted above for FIG. 1. However, in this embodiment, the less volatile GA isomers 128 (i.e., unreacted products being converted to the cis-6 isomer) are drawn out of the bottom of the first distillation column 126. These GA isomers 128 are then heated by any suitable means (not shown), and provided to a separate reactor, such as "Reactor 2" 229 (containing a suitable acid catalyst) where they are continuously interconverted to produce equilibrated GA isomers 230 which are added to the GA isomers 114 being provided to the first distillation column 126. Use of a separate "Reactor 2" 229 allows higher temperatures to be used, thus resulting in faster distillation, while still maintaining high yields.

Various embodiments further comprise a method 300 comprising combining 302 glycerol and acetaldehyde in a first reactor to produce glycerol acetal isomers, acetaldehyde and water; separating 304 the glycerol acetal isomers from the unreacted acetaldehyde and water in an evaporator; distilling 306 the glycerol acetal isomers in a vacuum distillation column with a Brønsted acid catalyst; removing 308 cis-5-hydroxy-2-methyl-1,3-dioxane isomer (cis-6 isomer) from the vacuum distillation column; oxidizing 310 the cis-6 isomer in a second reactor to produce 2-methyl-1,3-dioxan-5-one (G-tone); and combining 312 the G-tone with water in a reactive distillation column to produce 1,3-dihydroxyacetone (DHA) in an aqueous solution. In one embodiment the DHA is dried to produce pure DHA.

In one embodiment, the glycerol acetal isomers are continuously interconverted within the vacuum distillation column. In one embodiment, the method comprises removing less volatile glycerol acetal isomers from the reboiler of the vacuum distillation column; heating the less volatile glycerol acetal isomers to produce heated isomers; exposing the heated isomers to an acid catalyst in a third reactor to produce equilibrated isomers; and combining the equilibrated isomers with glycerol acetal isomers exiting the evaporator.

In one embodiment, the water and acetaldehyde are separated in a vaporizer using flash distillation. In one embodiment, the separated acetaldehyde is provided to the first reactor.

DHA is useful in a wide variety of applications. For example, DHA is known to have a non-toxic skin coloring effect. As such, DHA is the active ingredient in sunless tanning agents (typically in amounts from about two (2) wt % to about five (5) wt %), and may benefit patients suffering with vitilgo, an uneven pigmentation of the skin, by selectively tanning or darkening lighter skin areas. In one embodiment, a tanning composition providing an effective tanning amount of DHA produced according to the novel methods described herein, in combination with a carrier is provided as a tanning agent, wherein the composition is formulated to tan or selectively tan human skin. In one embodiment, the composition further includes additional components such as components to provide uniform application, skin conditioners, fragrances, anti-perspirants, and the like.

Additionally, when DHA is reacted with proline, a desirable aroma may be given to wine. DHA is also useful in various neutraceuticals. For example, DHA can be combined with pyruvic acid to produce 1,3-dihydroxyacetone pyruvic acid (DHAP), a "fat-burning" nutritional supplement typically administered orally, which may increase lean muscle mass. DHA is also used in fungicides, plasticizers and cosmetics.

The technology will be further described by reference to the following examples, which are offered to further illustrate the various embodiments described herein. It should be understood, however, that many variations and modifications may be made while remaining within the scope of the invention.

Example 1

Production of Cyclic Glycerol Acetals (GA) from Glycerol and 1,1-Diethoxyethane (DEE)

Unless otherwise indicated, all starting materials were obtained from Sigma-Aldrich. Gas chromatography (Perkin-Elmer Sigma 2000 gas chromatography (DB-Wax column)) was used to analyze the final products.

In a stainless steel reactor, 0.23 g of Amberlyst-15 cationic exchange resin (16-50 mesh was mixed with 23 g of anhydrous glycerol (99.5%, J. T. Baker) and 29.5 g of DEE (99%).

The mixture was stirred at 50° C. under atmosphere pressure. At the beginning, the mixture had two phases. As the reaction proceeded, it became a single phase. After 60 min, the conversion of glycerol was 94%. At 120 min, the conversion of glycerol was nearly 100%, with the selectivity to GA being greater than 90%.

After completion of the reaction, the catalyst and liquid were separated using vacuum filtration with an aspirator on a faucet and a Buchner funnel. The organic solution was then partially evaporated in a rotary evaporator at 70° C. under vacuum (−0.1 MPa). Volatile compounds such as ethanol and DEE were also removed in this process.

The final products comprised the four cyclic glycerol acetal (GA) isomers, namely, the cis-6 isomer, the trans-6 isomer, the cis-5 isomer, and the trans-5 isomer, together with water and acetaldehyde and trace amounts of glycerol.

Example 2

Production of GA from Glycerol and Acetaldehyde

Unless otherwise indicated, all starting materials and equipment are as noted in Example 1.

In a 75 ml Parr 5000 Multireactor System stainless steel reactor (Parr Instrument Co.), 0.14 g of Amberlyst-15 cationic exchange resin (16-50 mesh) was mixed with 13.8 g of anhydrous glycerol (99.5%, J. T. Baker) and 6.6 g of acetaldehyde (99%).

The mixture, which initially contained two phases, was stirred at 40° C. under atmospheric pressure, and converted to a single phase as the reaction proceeded. After approximately 120 min, the conversion of glycerol was 94%, and selectivity to GA was over 85%.

After completion of the reaction, the catalyst and liquid were separated with a Model WP-15 aspiration pump (Oakton Instruments) using a Buchner funnel. The organic solution was then partially evaporated in a Model RE 47 rotary evaporator (Yamato Scientific Co., Ltd.) at 70° C. under vacuum (−0.1 MPa). Volatile compounds such as water and acetaldehyde were also removed in this process.

The final product comprised the four cyclic GA isomers (GA) noted in Example 1.

Example 3

Production of Cis-6 from GA Using 3.6 m Distillation Column

Unless otherwise indicated, all starting materials and equipment used are as noted in Example 1.

GA was used to produce the cis-6 isomer in a batch vacuum distillation column. The column (height=3.6 m; inner diameter=50 mm) (hereinafter "3.6 m distillation column") was assembled in-house using conventional components purchased from various suppliers, such as Ace Glass. The 3.6 m distillation column was packed with PRO-PAK® Protruded Metal Distillation Packing (0.6 cm, 316 SS) from Scientific Development Co. (College Park, Tex.). Pressure was adjusted using a Model RV8 vacuum pump (Edwards).

800 ml of GA (produced according to the method described in Example 1) was fed into the reboiler portion of the 3.6 m distillation column) and heated slowly (at a rate of about two (2) to three (3)° C./min) to the desired temperature. When steady state was achieved throughout the column (as indicated by constant temperature in the reboiler and throughout the column), the top product (i.e., the cis-6 isomer), was withdrawn slowly, i.e., at a rate of about two (2) ml/min., and collected in 60 ml sample bottles. Table 1 provides the compositions of these samples, which comprise the four isomers noted in Examples 1 and 2 but initially enriched in the cis-6 isomer:

TABLE 1

Isomer Concentrations with 3.6 m Distillation Column

| Sample No. | Vapor Temp (° C.) | Pressure (mm Hg) | Composition (wt %) | | | |
|---|---|---|---|---|---|---|
| | | | cis-6 | cis-5 | trans-5 | trans-6 |
| 0* | | | 35 | 18 | 15 | 32 |
| 1 | 64 | 9 | 99 | 1 | 0 | 0 |
| 2 | 78 | 20 | 94 | 3 | 3 | 0 |
| 3 | 78 | 20 | 91 | 6 | 3 | 0 |
| 4 | 81 | 20 | 84 | 14 | 2 | 0 |
| 5 | 86 | 21 | 45 | 51 | 4 | 0 |
| 6 | 89 | 21 | 13 | 71 | 15 | 1 |
| 7 | 93 | 21 | 2 | 54 | 41 | 3 |
| 8 | 97 | 20 | 2 | 19 | 56 | 23 |
| 9 | 99 | 20 | 0 | 2 | 34 | 63 |
| 10 | 101 | 21 | 0 | 3 | 12 | 85 |
| 11 | 100 | 21 | 0 | 2 | 5 | 94 |
| 12 | 102 | 20 | 0 | 0 | 3 | 97 |

*Sample 0 is the mixture before distillation.

Example 4

Production of Cis-6 Isomer from GA Using 1.5 m Distillation Column

Unless otherwise noted, all starting materials and equipment are as noted in Examples 1-3.

GA was used to produce the cis-6 isomer in a batch vacuum distillation column. The column (height=1.5 m; inner diameter=50 mm) (hereinafter "1.5 m distillation column") was assembled in-house as described in Example 3, using the packing as described in Example 3.

1000 ml of GA (produced according to the method described in Example 1) was fed into the reboiler portion of the 1.5 m distillation column) and heated slowly (at a rate of about two (2) to three (3)° C./min) to the desired temperature in the presence of 50 mg of Amberlyst-15 cationic exchange resin (hereinafter "Amberlyst catalyst"). The Amberlyst catalyst rapidly interconverted the GA. When equilibrium was achieved throughout the column, the top product (cis-6 isomer) was withdrawn slowly, i.e., at a rate of about two (2) ml/min., and collected in 60 ml sample bottles.

Table 2 shows the results of 60 ml samples collected from the top of the 1.5 m distillation column. In one set of test conditions (at 50° C. under vacuum), the equilibrated GA contained 37% cis-6, 17% cis-5, 13% trans-5, and 33% trans-6 isomers by weight. At 60° C. and under vacuum, the equilibrium composition was 32% cis-6, 22% cis-5, 18% trans-5, and 28% trans-6.

TABLE 2

Isomer Concentrations using 1.5 m Distillation Column

| Sample No. | Vapor Temp (° C.) | Pressure (mm Hg) | Composition (wt %) | | | |
|---|---|---|---|---|---|---|
| | | | Cis-6 | cis-5 | trans-5 | Trans-6 |
| 0* | | | 32 | 22 | 18 | 28 |
| 1 | 50 | 4.2 | 99 | 1 | 0 | 0 |
| 2 | 51 | 4.4 | 95 | 3 | 2 | 0 |
| 3 | 51 | 4.2 | 97 | 2 | 1 | 0 |
| 4 | 50 | 4.2 | 93 | 4 | 2 | 1 |
| 5 | 50 | 4.3 | 93 | 4 | 2 | 1 |
| 6 | 51 | 4.3 | 90 | 5 | 4 | 1 |

*Sample 0 is the mixture in reboiler before distillation.

As Table 2 shows, all samples contained at least 90% of the cis-6 isomer. The total amount of the cis-6 isomer obtained from the partial distillation was 340 ml. However, it is expected that further distillation of the GA will lead to transformation of substantially all of the GA (the four isomers) into the desired cis-6 isomer. These results show that the Amberlyst catalyst is a highly effective catalyst for the transformation of the GA (isomer mixture) into the desired isomer, namely, the cis-6 isomer.

Example 5

Oxidation of Cis-6 Isomer to G-Tone with Pyridinium Chlorochromate (PCC)

Unless indicated, all starting materials and equipment are as indicated in the above Examples.

This testing was performed according to the method described in G. Piancatelli, et. al., "Pyridinium Chlorochromate: A Versatile Oxidant in Organic Synthesis," Synthesis, 1982, pp. 245-258 and 1164, which is incorporated herein by reference in its entirety.

In a 500 ml round bottomed flash fitted with a reflux condenser and magnetic stirrer, 32.5 g of pyridinium chlorochromate (PCC, >98%) was suspended in 200 ml of anhydrous dichloromethane (≥99.8). Cis-6 isomer (11.8 g, prepared using the methods described in Example 4) in dichloromethane (20 ml) was added to the magnetically stirred suspension. After 1.5 h, 200 ml of dry diethyl ether (anhydrous, ≥99.0%) was added and the supernatant organic solution was decanted.

The final product was analyzed using GC. The yield of G-tone was 30%.

Example 6

Production of G-Tone from Cis-6 Isomer Using Ruthenium Dioxide ($RuO_2$) and Potassium Bromate ($KBrO_3$)

Unless otherwise indicated, all starting materials and equipment are as indicated in the above Examples.

The cis-6 isomer was obtained using the methods described in Example 4). Ruthenium(IV) dioxide hydrate (0.26 g, $Ru_{O2} \cdot x_{H2}O$, water content=28%) was stirred into 10 ml of distilled water. Additionally, 0.4 g of cis-6 isomer ten (10) ml of saturated potassium bromated ($KBr_{O3}$, ≥99.8%) solution were added and stirred for 45 min at room temperature.

Two samples were taken at 20 and 45 min after the addition of GA for analysis. The yields of G-tone were 96% and >99%, respectively.

After the reaction, the ruthenium catalyst was separated by vacuum filtration using a Buchner funnel. The final product obtained was a colorless liquid solution, indicating that no soluble ruthenium species were formed in the process.

Example 7

Production of G-Tone from Cis-6 Isomer Using Ruthenium Tetraoxide ($RuO_4$)

Unless otherwise noted, all starting materials and equipment are as noted in Example 6.

Ruthenium (IV) dioxide hydrate (0.30 g) was stirred into ten (10 ml) of distilled water. Thereafter, five (5) g of sodium hypochlorite solution (NaClO, 10-15%) was added dropwise to produce ruthenium tetraoxide ($RuO_4$). Thereafter, ten (10) g of 4% cis-6 isomer in distilled water was added to produce G-tone. The entire process was carried out at room temperature and atmospheric pressure.

Two samples were taken for analysis at 50 and 70 min after the addition of the cis-6 isomer solution. The yield of G-tone was 77% and 78%, respectively.

Another five (5) g of the same NaClO solution was added after the samples were taken. After approximately 20 minutes, the yield of G-tone improved to 93.5%.

After completion of the reaction, the catalyst and liquid were separated by vacuum filtration using a Buchner funnel. The liquid phase was dark green in color, indicating the formation of perruthenate ($RuO_4^-$) species, which is a byproduct produced in the process of making $RuO_4$.

Example 8

Production of G-Tone from Cis-6 Isomer Using a Pt—Bi/C Catalyst

Unless otherwise noted, all starting materials and equipment are as noted in Example 6.

The cis-6 isomer (4 g) and Pt—Bi/C catalyst (0.25 g, 5% Pt and 1% Bi, Johnson Matthey Co.) were stirred into 36 g of distilled water. Sodium hydroxide (NaOH, >99%, J. T. Baker) solution (1 mol/L) was added to adjust the pH to a value between 11 and 12. The mixture was then heated to 60° C. under atmospheric pressure with pure oxygen gas passed through it (flow rate=30 ml/min).

After about three (3) hours, the yield of G-tone was approximately six (6)% of the theoretical value, with a small amount (<1%) of glycerol and acetic acid produced as byproducts via acetal hydrolysis and acetaldehyde oxidation.

The reaction was run overnight. After about 20 hours, the conversion of the cis-6 isomer was 90%. Thereafter, 50% of the cis-6 isomer was hydrolyzed to glycerol and acetaldehyde, with the acetaldehyde further oxidized to acetic acid. The yield of G-tone was approximately 30% of the theoretical maximum.

Example 9

Production of G-Tone from Cis-6 Isomer Using a Pt/Al$_2$O$_3$ Catalyst

Unless otherwise noted, all starting materials and equipment are as noted in Example 6.

Pt/Al$_2$O$_3$ (0.51 g, 5% Pt, 325 mesh) catalyst was added to an aqueous cis-6 isomer solution (cis-6 5.92 g, water 30 ml). Thereafter, the mixture was heated to 65° C. under atmospheric pressure while air was passed through it (flow rate=28 ml/min).

After approximately 18 hours, the yield of G-tone was approximately four (4) % of theoretical.

Example 10

Production of G-Tone from Cis-6 Isomer Using Ruthenium (III) Trichloride and NaIO$_4$ Unless otherwise noted, all starting materials and equipment are as noted in previous examples.

Ruthenium (III) trichloride (0.3 g, Reagent Plus, Ru %=46% by wt) was stirred into ten (10 ml) of distilled water for approximately five (5) minutes. Thereafter, 0.4 g of the cis-6 isomer solution and ten (10) ml of saturated sodium periodate (NaIO$_4$, >99.8%) solution were added and stirred with the mixture. The entire process was carried out at room temperature.

Two samples were taken for GC analysis at 20 and 75 min after the addition of the cis-6 isomer. The results indicated that the yields of G-tone were 83% and nearly 88%, respectively.

In this reaction, part of the ruthenium catalyst dissolved in the reaction mixture, as evidenced by the red-brown color of the final solution. Vacuum filtration (Buchner filter) did not recover all the ruthenium catalyst.

Example 11

Production of G-Tone from Cis-6 Isomer Using Ruthenium (III) Trichloride and KBrO$_3$ Unless otherwise noted, all starting materials and equipment are as noted in previous examples.

Ruthenium(III) trichloride (0.30 g) was stirred into ten (10) ml of water for approximately five (5) minutes. Thereafter, 0.4 g of cis-6 isomer and ten (10) ml of saturated potassium bromated (KBrO$_3$) solution were added and stirred with the mixture for approximately 80 min. The entire process was carried out at room temperature.

Three samples were taken for GC analysis at 20, 40 and 75 min after the addition of the cis-6 isomer. The results indicated that the yield of G-tone were 90%, 94% and 95%, respectively.

In this reaction, the ruthenium species was entirely dissolved in the reaction mixture and formed a red-brown solution; no solid catalyst remaining after vacuum filtration (Buchner filter).

Example 12

Production of G-Tone from Cis-6 Isomer Using Ruthenium Dioxide and KBrO$_3$

Unless otherwise noted, all starting materials and equipment are as noted in previous examples.

G-tone was produced from the cis-6 isomer using a catalytic amount of ruthenium dioxide (RuO$_2$) and potassium bromate (KBrO$_3$). In this example, ruthenium (IV) dioxide hydrate (0.40 g) was stirred into ten (10) ml of water for approximately five (5) minutes. Thereafter, four (4) g of cis-6 isomer and 100 ml of saturated potassium bromate (KBrO$_3$) solution were added and stirred for 30 min. The entire process was carried out at room temperature.

After 20 minutes, a sample was taken for GC analysis and the yield of G-tone was 97%.

After completion of the reaction, the catalyst and liquid were separated by vacuum filtration using a Buchner funnel. The solution was dark green in color, indicating the presence of perruthenate species.

Example 13

Prophetic

In this testing, after the cis-6 isomer is oxidized, the reaction mixture, which will contain distilled water, G-tone, and inorganic salts (e.g., KBr), as well as other side products, such as acetaldehyde and acetic acid, will be subjected to a variety of acid catalysts, for production of DHA.

Thereafter, water and other volatile compounds will be removed using vacuum evaporation. At the same time, in some testing, the catalyst and inorganic salts will precipitate and will be filtered from the solution. The remaining liquid is expected to be highly-concentrated G-tone, i.e., in a concentration of about 50% or higher, up to 60%, 70%, 80%, 90%, 99% or higher, including quantitative amounts.

Since DHA is produced by dissolving the concentrated G-tone into water to form a solution, the addition of a Brønsted acid catalyst will produce a hydrolysis reaction as shown in Scheme IV.

DHA will be produced by dissolving the concentrated G-tone into distilled water and adding an acid catalyst to this solution, thus allowing the reaction shown in Scheme IV to occur.

By using an excess amount of water, it is expected that substantially all G-tone will be converted to DHA. After completion of the reaction, the byproducts, including water and acetaldehyde, will be removed by distillation.

It is expected that DHA will be recovered in amounts higher 50%, including up to 90% or higher, up to quantitative further including any ranges there between.

Example 14

Prophetic

One alternative approach for obtaining the DHA product is to hydrolyze G-tone before isolating it from the reaction mixture containing the catalyst and inorganic salt or salts. Following hydrolysis, the product DHA can then separated from the reaction mixture.

In this testing, after oxidation of the cis-6 isomer, an acid catalyst (as solid or soluble material) and excess distilled water will be added to the reaction mixture to carry out hydrolysis of G-tone. When hydrolysis is finished, water and other volatile compounds will be removed using vacuum evaporation. At the same time, solid DHA, catalyst and inorganic salt will be obtained.

In this mixture, DHA will be extracted into an organic solvent such as ethanol, acetone, cyclohexanone, a substituted cyclohexanone, or similar compounds. Other species (catalyst, salts, acid) become solids and will be removed by filtration. The extracted DHA solution will be distilled to remove the solvent and recover pure DHA.

It is expected that DHA will be recovered in amounts higher than 50%, including up to 90% or higher, further including any ranges there between.

CONCLUSION

The novel methods described herein provide relatively quick, environmentally safe and economical routes for producing and/or recovering DHA. As a result, energy consumption is reduced. In one embodiment, the novel methods can be used as an alternative to fermentation for the production of DHA. In one embodiment, a continuous process is used. The various DHA-containing products, e.g., sunless tanning products, can now also be produced faster and more economically.

Although specific embodiments have been illustrated and described herein, it will be appreciated by those of ordinary skill in the art that any procedure that is calculated to achieve the same purpose may be substituted for the specific embodiments shown. For example, although the methods discussed focused primarily on acetaldehyde, it is to be understood that other reactants may also be used with glycerol in the formation of DHA, including, but not limited to, 1,1-diethoxyethane (See Example 1). This disclosure is intended to cover any adaptations or variations of the present subject matter. Therefore, it is manifestly intended that embodiments described herein be limited only by the claims and the equivalents thereof.

What is claimed is:

1. A method comprising:
   reacting glycerol with acetaldehyde or 1,1-diethoxyethane to produce 1,3-dihydroxyacetone (DHA), wherein the method comprises:
   with an acid catalyst, forming glycerol acetal isomers from the glycerol and acetaldehyde or 1,1diethoxyethane, wherein at least one of the glycerol acetal isomers is a cis-5-hydroxy-2-methyl-1,3-dioxane isomer (cis-6 isomer);
   separating the cis-6 isomer from the glycerol acetal isomers;
   with an oxidation catalyst, oxidizing the cis-6 isomer to produce 2-methyl-1,3-dioxan-5-one (G-tone); and
   combining the G-tone with water to produce 1,3-dihydroxyacetone (DHA), wherein the DHA is produced without using fermentation or direct oxidation of the glycerol.

2. The method of claim 1 wherein conversion of glycerol to DHA is at least 94%.

3. The method of claim 2 wherein the conversion is nearly 100%.

4. The method of claim 1 wherein the acid catalyst is a sulfuric acid catalyst.

5. The method of claim 1 wherein the glycerol acetal isomers further comprise trans-5-hydroxy-2-methyl-1,3-dioxane (trans-6 isomer), cis-4-hydroxymethyl-2-methyl-1,3dioxolane (cis-5 isomer), and/or trans-4-hydroxymethyl-2-methyl-1,3-dioxolane (trans-5 isomer), wherein the method further comprises converting the trans-6 isomer, the cis-5 isomer, the trans-5 isomer, or combinations thereof, to the cis-6 isomer.

6. The method of claim 1 wherein the oxidation catalyst is a homogeneous catalyst.

7. The method of claim 1 wherein the oxidation catalyst is a heterogeneous catalyst.

8. The method of claim 1 wherein the oxidation catalyst is a ruthenium catalyst, a palladium catalyst or a platinum catalyst.

9. The method of claim 8 wherein the ruthenium catalyst is a ruthenium (III) trichloride catalyst, a ruthenium dioxide catalyst, or a ruthenium tetraoxide catalyst.

10. The method of claim 8 wherein the oxidizing step further comprises adding an oxidizer.

11. The method of claim 10 wherein the oxidizer is selected from $KBrO_3$, $NaBrO_3$, $NaClO$, $Ca(ClO)_2$ and $NaIO_4$.

12. The method of claim 1 further comprising hydrolyzing and separating the G-tone to produce the DHA.

13. A method comprising:
   combining glycerol and acetaldehyde in a first reactor to produce glycerol acetal isomers and water together with unreacted acetaldehyde;
   separating the glycerol acetal isomers from the unreacted acetaldehyde and water in an evaporator;
   distilling the glycerol acetal isomers in a vacuum distillation column with an acid catalyst; removing cis-5-hydroxy-2-methyl-1,3-dioxane isomer (cis-6 isomer) from the vacuum distillation column;
   oxidizing the cis-6 isomer in a second reactor to produce 2-methyl-1,3-dioxan-5-one (G-tone); and
   combining the G-tone with water in a reactive distillation column to produce 1,3dihydroxyacetone (DHA).

14. The method of claim 13 wherein the glycerol acetal isomers are continuously interconverted within the vacuum distillation column.

15. The method of claim 14 further comprising:
   removing less volatile glycerol acetal isomers from the vacuum distillation column;
   heating the less volatile glycerol acetal isomers to produce heated isomers;
   exposing the heated isomers to an acid catalyst in a third reactor to produce equilibrated isomers; and
   combining the equilibrated isomers with the glycerol acetal isomers exiting the evaporator.

16. The method of claim 15 wherein the unreacted acetaldehyde and water are separated in a vaporizer using flash distillation.

17. The method of claim 16 wherein separated acetaldehyde is provided to the first reactor.

18. The method of claim 1 wherein the acid catalyst is a Brønsted acid catalyst.

19. The method of claim 1 wherein the acid catalyst is a cationic exchange resin.

20. The method of claim 1 wherein the oxidation catalyst is a chromium-based catalyst.

21. The method of claim 19 wherein the chromium-based catalyst is pyridinium chlorochromate.

22. The method of claim 8 wherein the platinum catalyst is a Pt—Bi/C catalyst or a Pt/Al$_2$O$_3$ catalyst.

23. The method of claim 1 wherein the DHA is produced in a batch process in less than 20 hours.

24. The method of claim 1 further comprising drying the DHA to produce substantially pure DHA.

25. The method of claim 1 wherein a yield of G-tone is from about 50% to about 99% of theoretical yield.

26. The method of claim 25 wherein the yield is from about 77% to about 97%.

27. The method of claim 1 wherein the DHA is useful as a sunless tanning agent.

28. The method of claim 1 wherein the DHA is useful in wine, neutraceuticals, nutritional supplements, fungicides, plasticizers, cosmetics and combinations thereof.

* * * * *

UNITED STATES PATENT AND TRADEMARK OFFICE
CERTIFICATE OF CORRECTION

PATENT NO. : 8,735,633 B2  
APPLICATION NO. : 13/183114  
DATED : May 27, 2014  
INVENTOR(S) : Dennis Miller et al.

Page 1 of 1

It is certified that error appears in the above-identified patent and that said Letters Patent is hereby corrected as shown below:

On the Title Page

Item (56) Other Publications/Col. 2/Line 12: Error reads as "Dihydroxyactone" and should read as "Dihydroxyacetone"

In the Specification

Col. 7/Line 6: Error reads as "vitilgo" and should read as "vitiligo"

Col. 10/Line 22: Error reads as "Ru$_{O2}$.x$_{H2}$O" and should read as "RuO$_2$.xH$_2$O"

Col. 10/Line 24: Error reads as "KBr$_{O3}$" and should read as "KBrO$_3$"

In the Claims

Col. 13/Line 56: Error reads as "1,1diethoxyethane," and should read as "1,1-diethoxyethane,"

Col. 14/Line 9-10: Error reads as "1,3dioxolane" and should read as "1,3-dioxolane"

Col. 14/Line 44: Error reads as "1,3dihydroxtacetone" and should read as "1,3-dihydroxtacetone"

Signed and Sealed this  
Twenty-sixth Day of August, 2014

Michelle K. Lee  
*Deputy Director of the United States Patent and Trademark Office*